| United States Patent [19] | [11] Patent Number: 4,576,645 |
|---|---|
| Ravel et al. | [45] Date of Patent: Mar. 18, 1986 |

[54] WHIPPED GEL COMPOSITION

[75] Inventors: Kanak K. R. Ravel, Perth Amboy; Bhupendra R. Vaidya, Kendall Park; Nelly A. Nerizon, Belleville, all of N.J.

[73] Assignee: Block Drug Co., Inc., Jersey City, N.J.

[21] Appl. No.: 678,697

[22] Filed: Dec. 6, 1984

[51] Int. Cl.$^4$ .................. A01N 31/00; A61F 13/00; A23C 11/00; A61K 9/10
[52] U.S. Cl. .................. 106/125; 106/128; 106/131; 106/132; 252/304; 252/310; 252/311; 252/312; 252/315.01; 252/315.1; 252/315.3; 252/315.4; 426/573; 514/944; 514/786; 514/779; 514/774; 514/777; 514/289; 514/357; 514/653
[58] Field of Search .............. 424/360, 361, 362, 363, 424/365; 426/573; 106/125, 131, 132, 128; 252/304, 310, 311, 312, 315.01, 315.4, 315.3, 315.1

[56] References Cited

U.S. PATENT DOCUMENTS

| 2,373,727 | 4/1945 | West et al. | 106/132 |
|---|---|---|---|
| 3,395,236 | 7/1968 | White | 424/360 |
| 3,398,007 | 8/1968 | Pillersdorf et al. | 106/128 |
| 3,767,784 | 10/1973 | Gluck | 424/28 |
| 3,984,571 | 10/1976 | Chen | 424/360 |
| 4,146,652 | 3/1979 | Kahn et al. | 426/573 |
| 4,305,933 | 12/1981 | Wiczer | 424/34 |
| 4,312,891 | 1/1982 | Eisfeldt | 426/573 |
| 4,388,307 | 6/1983 | Cavanak | 424/365 |
| 4,388,337 | 6/1983 | Cawdron | 426/573 |
| 4,414,236 | 11/1983 | Moran et al. | 426/573 |

Primary Examiner—Ronald W. Griffin
Attorney, Agent, or Firm—Ostrolenk, Faber, Gerb & Soffen

[57] ABSTRACT

A thixotropic, spoonable soft gel in an aerated or non-aerated multiphase composition of emulsified glycerides dispersed in a continuous phase of hydrocolloid and has an RVT Brookfield viscosity of about 100,000-500,000 centipoises at room temperature and a TD spindle speed of 2.5 rpm.

23 Claims, No Drawings

WHIPPED GEL COMPOSITION

BACKGROUND OF THE INVENTION

The currently marketed oral liquids such as cough syrups, analgesics, antacids, laxatives and the like, generally contain an active drug or a combination of active drugs and various pharmaceutical carrier materials such as diluents, suspending agents, solvents, flavors, and the like which have been combined to form a vehicle suitable for dispensing in liquid form. The liquid form can be, if desired, a suspension or an emulsion.

Parents have generally experienced three principle problems in using elixirs, syrups, suspensions, emulsions and similar liquids which are designed for administration to children. Firstly, the liquid has a tendency to spill from the administration device, usually a spoon, resulting in a sticky mess and possible causing staining of clothing, furniture and the like. Secondly, many medicines require that only a portion of the administration device, e.g. a portion of a teaspoon, be the adminstrated dosage for very young children. As a result, there is difficulty in measuring the exact dosage to be administered.

The third principle problem is that children generally do not like the taste of the medicine. Many of the active ingredients used in the pharmaceutical industry today are organo-metallics, amines, amides, alkaloids, and their derivatives. These agents are known to impart unpleasant, bitter, metallic or other characteristic tastes or aftertastes to conventionally formulated pharmaceutical dosage forms.

In some instances, medicaments have been incorporated into gelled vehicles. See, e.g., U.S. Pat. Nos. 3,767,784 and 4,305,933. Such compositions do not overcome the foregoing problems and do not provide a convenient, pleasant tasting dosage form which is appealing to all age groups as a vehicle for taking medicine.

It is accordingly the object of this invention to provide a unique, novel and pleasant tasting composition which is useful as a confectionery or alternatively is useful as a carrier for a convenient drug delivery system which overcomes difficulties realized with children's liquid medications heretofore. This and other objects of the invention will become apparent to those skilled in the art from the following detailed description.

SUMMARY OF THE INVENTION

This invention relates to a unique, novel, pleasant tasting composition which is useful as a confectionery or alternatively is useful as a carrier for a convenient drug delivery system which is particularly suitable for use with children, for example, one which is thick and smooth enough so that it will not spill off a spoon before reaching an infant's mouth to deliver the exact dosage desired. More particularly, the invention provides a thixotropic, spoonable soft gel which is an aerated or non-aerated multiphase composition of emulsified glycerides dispersed in a continuous hydrocolloid phase, the gel having an RVT Brookfield viscosity of about 100,000-500,000 cps at room temperature and a TD spindle speed of 2.5 rpm.

DESCRIPTION OF THE INVENTION

The thixotropic, spoonable soft gel of the present invention is an aerated or non aerated multiphase composition of emulsified glycerides dispersed in a continuous hydrocolloid phase. The gel, i.e., the aerated or non aerated composition, has an RVT Brookfield viscosity of at least about 100,000 centipoises, preferably about 100,000–500,000 centipoises, at room temperature and a TD spindle speed of 2.5 revolutions per minute.

The glycerides used in the present invention can be fats or fat derivatives derived from any source. Thus, for example, typical glycerides can be derived from palm oil, soybean oil, cottonseed oil, peanut oil, corn oil and the like. Similarly, alcohol esters such as propylene glycol monoesters of hydrogenated soyabean oil can also be used. The glycerides employed are preferably monoglycerides but some or all of the glyceride component of the soft gel can be a di- or polyglyceride. In general, the glyceride component will be about 3–15 weight percent of the thixotropic, spoonable soft gel and preferably about 4–8 percent of the gel weight.

In some cases, the glycerides may be self-emulsifiable in the hydrocolloid. One or a mixture of emulgants can be used, if desired, in such a system. When non self-emulsifying glycerides are employed, the emulgants used to emulsify the glycerides can be one or more of any of the emulgants previously used to emulsify glycerides. Examples of such emulgants include sorbitan monooleate, sorbitan monostearate, lecithin, and the like. Since the soft gel of the present invention is intended to be ingested, the emulgant and the other ingredients in the gel should be non-toxic. The emulgants, when employed, will generally be about 0.25–5 weight percent of the gel and preferably about 0.35–0.45 percent of the total weight.

Any non-toxic hydrocolloid can be used to form the continuous phase of the multiphase composition of the present invention. Typical hydrocolloids include xanthan gum, alginates, carageenan, sodium carboxymethyl cellulose, methylcellulose, various starches (including modified food starches), locust bean gum, gelatin and the like. The hydrocolloids are generally low density and relatively low viscosity (on the order of about, for example, 8,000 centipoises) and therefore on a weight basis, they constitute about 0.4–1 percent of the gel. Preferably, the hydrocolloid is about 0.5 to 0.8 weight percent of the composition.

A significant portion of the spoonable, soft gel of the present invention is constituted by a bulking agent and, for this purpose, any bulking agent which has heretofore been used in food products can be employed. Typical examples include sucrose, sorbitol, corn syrup solids and other polysaccharide bulking agents. In general, the bulking agent will constitute about 30–60 percent of the soft gel, preferably about 35–45 percent of the total weight.

In order for proper gelling to be effected, a food acid is included in the thixotropic, spoonable soft gel. Such food acids include adipic acid, malic acid, fumaric acid, citric acid and the like which are usually present in an amount from about 0.1–1.5 percent of the gel and preferably about 0.5–1 percent.

If desired, the gel may also include one or more sweeteners or artificial sweeteners such as sodium, calcium or ammonium saccharin salts, cyclamates, aspartame, glycyrrhizin, preservatives such as sodium benzoate, sequestering agents such as sodium hexametaphosphate, calcium salts, colorants and flavorants. Suitable flavors which can be used include the citrus oils such as lemon, orange, lime and grapefruit and fruit essences such as apple, pear, peach, strawberry, raspberry, cherry, plum, pineapple and banana essence, as well as the essential oils such as peppermint, spearmint, anise, eucalyptus, cinnamon, cassia and methyl salicylate. Various synthetic flavors such as mixed fruit can also be used. In general, each of such additional optional ingredients will constitute up to about 0.25 percent of the gel.

The balance of the gel is water and generally the amount of water will be about 30–65 weight percent and preferably about 50–60 weight percent.

The thixotropic, spoonable soft gel of the present invention can be prepared by hydrating the hydrocolloids in the water at any convenient temperature, preferably at room temperature. The bulking agent is then added and dissolved with stirring and heating, if necessary. Separately, a glyceride phase and the emulgants when employed, is prepared. The glyceride phase is liquified by heating to slightly above its melting point and then added to the hydrated hydrocolloid containing dissolved bulking agent and dispersed therein. Preferably, the dispersion step is effected using a high shear type of mixer. The mixture is then cooled to about room temperature and the various auxiliary ingredients, e.g. colors and flavors and food acids, are added and mixed therein. When the gel is to be used as a medicament carrier, the medicament is preferably added after the composition has been cooled in order to avoid any heat denaturing of the active drug. However, the drug(s) and auxiliary ingredients can be added at any temperature where they are stable, if so desired.

The gel product has an RVT Brookfield viscosity of about 100,000–500,000 centipoises at room temperature and a TD spindle speed of 2.5 rpm, preferably about 100,000–300,000 cps. The pH of the gel product is generally not more than about 7.0, preferably about 3.0–4.5.

The dispersion is aerated by whipping, beating or otherwise blowing an aerating agent through the gelled mixture in order to increase the volume of the gel by about 10–60 percent, i.e. an about 10–60 percent "overrun". Preferably, the overrun is about 10–30%. Purified air, carbon dioxide or nitrogen can be used for this purpose. The aeration can be effected at any temperature which does not denature the dispersion or its ingredients and generally, temperatures of about 15°–100° C., preferably about 22° C.–30° C. can be used. The duration and speed of the aeration is adjusted so that the desired final consistency is attained. The aeration time may, for example, vary from one minute to several hours, although a period of about 10–15 minutes is often satisfactory. The aeration step can be effected at any point after the emulsified glyceride and hydrocolloid phases have been combined, e.g., simultaneously with or after the addition of the medicament and auxiliary ingredients. Preferably, it is effected after such addition. The aerated product has a texture that is creamy, smooth and spoonable.

As used herein, the term "drug" or medicament broadly includes, without limitation, physiologically or pharmacologically active substances for producing a localized or systemic effect or effects in animals, and in human beings. The active drugs that can be administered by the gel delivery product of the invention include, without limitation: laxatives, such as phenolphthalein, bisacodyl, casanthranol, etc.; antacids, such as calcium carbonate, magnesium-aluminum hydroxide gel, magnesium trisilicate; drugs acting on the central nervous system such a hypnotics and sedatives, such as pentorbarbital sodium, phenobarbital, secobarbital, thiopental, etc.; heterocyclic hypnotics such as dioxopiperidines and glutarimides; hypnotics and sedatives such as amides and ureas exemplified by diethylisovaleramide and $\alpha$-bromoisovaleryl urea and the like; hypnotics and sedative alcohols such as carbomal, naphthoxyethanol, methylparaphenol and the like; and hypnotic and sedative urethans, disulfanes and the like; psychic energizers such as isocarboxacid, nialamide, phenelzine, imipramine, tranylcypromine, pargylene and the like; tranquilizers such as chloropromazine, promazine, fluphenazine, reserpine, deserpidine, meprobamate, benzodiazepines such as chlordiazepoxide and the like; anticonvulsants such as primidone, diphenylhydantoin, ethotoin, pheneturide, ethosuximide and the like; muscle relaxants and antiparkinson agents such as mephenesin, methocarbomal, trihexylphenidyl, biperiden, levo-dopa, also known as L-dopa and 1-$\beta$-3, 4-dihydroxyphenylalanine, and the like; analgesics such as morphine, codeine, meperidine, nalorphine and the like; anti-pyretics and anti-inflammatory agents such as aspirin, acetaminophen, ibuprofen,, salicylamide, sodium salicylate and the like; local anesthetics such as procaine, lidocaine, naepaine, piperocaine, letracaine, dibucaine, and the like; antispasmodics and antiulcer agents such as atropine, scopolamine, methscopolamine, oxyphenonium, papaverine, prostaglandins such as $PGE_1$, $PGE_2$, $PGF_{2\alpha}$, $PGF_{3\alpha}$, PGA and the like; antimicrobials such as pencillin, tetracycline, oxytetracycline, chlorotetracycline, chloramphenicol, sulfonamides and the like; antimalarials such as 4-aminoquinolines, 8-aminoquinolines and pyrimethamine; hormonal agents such as prednisolone, cortisone, cortisol and triamcinoline; androgenic steroids, for example, methyltestosterone, fluoximesterone and the like; estrogenic steroids, for example, 17$\beta$-estradiol and ethinyl estradiol; progestational steroids, for example, 17$\alpha$-hydroxyprogesterone acetate, 19-nor-progesterone, norethindrone and the like; sympathomimetic drugs such as epinephrine, amphetamine, ephedrine, norepinephrine and the like; cardiovascular drugs, for example, procainamide, amyl nitrate, nitroglycerin, dipyridamole, sodium nitrate, mannitol nitrate and the like; diuretics, for example, chlorothiazide, flumethiazide and the like; antiparasitic agents such as bephenium hydroxynaphthoate and dichlorophen, dapsone and the like; neoplastic agents such as mechlorethamine, uracil mustard, 5-fluorouracil, 6-thioquanine, procarbazine and the like; hypoglycemic drugs such as insulins, protamine zinc insulin suspension, and other art known extended insulin suspension; sulfonylureas such as tolbutamide, acetohexamide, tolazamide, and chlorpropamide, the biguanides and the like; nutritional agents such as vitamins, essential amino acids, essential fats and the like; and other physiologically or pharmacologically active agents. Also, the drugs can be present as the pharmacologically acceptable derivaties, such as ethers, esters, amides, acetals, etc. that lend themselves to passage into the circulatory system.

In order to further illustrate the present invention, various examples are set forth below. In these examples, as throughout this specification and claims, all temperatures are in degrees centigrade and all parts and percentages are by weight unless otherwise specified.

EXAMPLE 1

A mixture of 0.1 part xanthan gum and 0.7 part alginates and 52.453 parts of water was prepared and 40 parts of sucrose was dissolved therein at 25° C. with stirring. Separately, a glyceride oil phase was prepared by providing 5 parts of monoglycerides (Myverol 18-07) and 0.5 part of Polysorbate 60. The glyceride phase was heated to about 78° C. and added to the xanthan/alginate/sucrose solution in a high shear mixer. After the glyceride phase had been dispersed in the hydrocolloid solution, the dispersion was allowed to cool to room temperature. Thereafter, 0.2 part of sodium hexametaphosphate, 0.04 part of tricalcium phosphate, 1 part of adipic acid, 0.1 part of sodium benzoate, 0.045 part of dextromethorphan HBr, 0.01 part flavor and 0.005 part color was added and the mixture was aerated to about 10 volume percent overrun by blowing purified air therethrough.

EXAMPLE 2

A hydrated bulking agent-hydrocoloid solution was prepared by mixing 35 parts of sorbitol, 0.2 part of xanthan gum, 0.5 part of sodium carboxymethyl cellulose and 57.0076 parts of water. A glyceride phase of 6 parts of propylene glycol monoesters was added to the solution slightly above the melting point of the glyceride phase using a high shear type mixer. The composition was cooled to room temperature and then 0.01 part of sodium saccharin, 0.045 part of dextromethorphan HBr, 0.1174 part phenylpropanolamine HCl, 0.019 part chlorpheniramine maleate, 0.1 part sodium benzoate, 0.5 part malic acid, 0.02 part flavor and 0.005 part color was added. Unlike Example 1, the mixture was not aerated.

EXAMPLE 3

A mixture 47.6686 parts of water, 0.15 part xanthan gum, 0.4 part alginate and 45 parts of sucrose was prepared. A glyceride phase of 4 parts hydrogenated vegetable oil and 0.4 part sorbitan monooleate was added to the solution slightly above the melting point of the glyceride phase in a high shear mixer. The resulting mixture was cooled to room temperature and then 0.91 part guaifenesin, 0.045 part dextromethorphan HBr, 0.1174 phenylpropanolamine HCl, 0.75 adipic acid, 0.1 part sodium benzoate, 0.05 part flavor and 0.004 part color was added and the composition aerated as described in Example 1. The resulting thixotropic, spoonable soft gel had a viscosity greater than 100,000 centipoises, a pH of less than 5.0 and a texture which was creamy, smooth and spoonable.

EXAMPLES 4-6

Leveled spoonful of each of the aerated products of Examples 1 and 3 and the non-aerated product of Example 2 were inverted. There was no evidence of spillage after 15 minutes.

EXAMPLES 7-9

The procedures of Examples 1-3 are repeated omitting the medicament and increasing the amount of water by the weight of the omitted medicament. Thixotropic, soft gel confectioneries are thus prepared.

Various changes and modifications can be made in the products and process of this invention without departing from the spirit and scope thereof. The various embodiments which have been set forth herein were for the purpose of further illustrating the invention but were not intended to limit it.

What is claimed is:

1. An edible thixotropic, spoonable soft gel comprising an aerated multiphase composition of emulsified glyceride dispersed in a continuous hydrocolloid phase, said gel having an RVT Brookfield viscosity of about 100,000-500,000 centipoises at room temperature and a TD spindle speed of 2.5 rpm.

2. The spoonable soft gel of claim 1 in which said composition comprises about 30-65 percent water, about 3-15 percent glyceride and about 0.4-1 percent hydrocolloid.

3. The spoonable soft gel of claim 2, wherein said composition contains about 30-60 percent bulking agent, about 0.25-5 percent emulgant and has been aerated to about 10-60 volume percent overrun.

4. The spoonable soft gel of claim 3, wherein said composition comprises about 50-60 percent water, about 35-45 percent bulking agent, about 4-5 percent glycerides, about 0.35-0.45 percent emulgant and about 0.5-0.8 percent hydrocolloid.

5. The spoonable soft gel of claim 4, wherein said composition contains medicament.

6. The spoonable soft gel of claim 5, wherein said medicament is dextromethorphan HBr, chlorpheniramine maleate, phenylpropanolamine hydrochloride, guaifenesin, phenylephrine hydrochloride or pseudoephedrine hydrochloride or mixtures thereof.

7. The spoonable soft gel of claim 6, wherein said glyceride is a monoglyceride.

8. The spoonable soft gel of claim 1, wherein said composition contains a medicament.

9. The spoonable soft gel of claim 8, wherein said glyceride is a monoglyceride.

10. An edible thixotropic, spoonable soft gel comprising a multiphase composition of emulsified glyceride dispersed in a continuous hydrocolloid phase, having an RVT Brookfield viscosity of about 100,000-500,000 centipoises at room temperature and a TD spindle speed of 2.5 rpm.

11. The spoonable soft gel of claim 10 in which said composition comprises about 30-65 percent water, about 3-15 percent glyceride and about 0.4-1 percent hydrocolloid.

12. The spoonable soft gel of claim 11, wherein said composition contains about 30-60 percent bulking agent and about 0.25-5 percent emulgant.

13. The spoonable soft gel of claim 12, wherein said composition comprises about 50-60 percent water, about 35-45 percent bulking agent, about 4-5 percent glyceride, about 0.35-0.45 percent emulgant and about 0.5-0.8 percent hydrocolloid.

14. The spoonable soft gel of claim 12, wherein said composition contains medicament.

15. The spoonable soft gel of claim 14, wherein said medicament is dextromethorphan HBr, chlorpheniramine maleate, phenylpropanolamine hydrochloride, guaifenesin, phenylephrine hydrochloride or pseudoephedrine hydrochloride or mixtures thereof.

16. The spoonable soft gel of claim 14, wherein said glyceride is a monoglyceride.

17. The spoonable soft gel of claim 10, wherein said composition contains a medicament.

18. The spoonable soft gel of claim 17, wherein said glyceride is a monoglyceride.

19. An edible, thixotropic, spoonable soft gel comprising a multiphase composition of emulsified glyceride dispersed in a continuous hydrocolloid phase, said composition containing a medicament, said gel having an RVT Brookfield viscosity of about 100,000-500,000 centipoises at room temperature and a TD spindle speed of 2.5 rpm, said gel having a pH of not more than 7, said gel consisting essentially of about 30-65% water, about 30–60% bulking agent, about 3–15% glyceride, about 0.4–1% hydrocolloid, about 0.1–1.5% food acid and up to about 5% emulgant.

20. The spoonable soft gel of claim 19, wherein said gel consists essentially of about 50–60% water, about 35–45% bulking agent, about 4–5% glyceride, about 0.25–5% emulgant, about 0.5–0.8% hydrocolloid and about 0.5–1% food acid, wherein said viscosity is about 100,000–300,00 centipoises, said pH is about 3.0–4.5, and wherein said composition has been aerated to about 10–60 volume percent overrun.

21. The spoonable soft gel of claim 20 wherein said glyceride is a monoglyceride, said medicament is dextromethorphan HBr, chlorpheniramine maleate, phenylpropanolamine hydrochloride, guaifenesin, phenylephrine hydrochloride or pseudoephedrine hydrochloride or mixtures thereof, and wherein said overrun is about 10–30%.

22. The spoonable soft gel of claim 20 wherein said hydrocolloid is a mixture of xanthan and alginate, said bulking agent is sucrose, said food acid is adipic acid, and said glyceride is a monoglyceride or hydrogenated vegetable oil.

23. The spoonable soft gel of claim 20 wherein said hydrocolloid is a mixture of xanthan and sodium carboxymethyl cellulose, said bulking agent is sorbitol, said glyceride is propylene glycol monoester and said food acid is malic acid.

* * * * *